(12) United States Patent
Martin et al.

(10) Patent No.: US 7,603,192 B2
(45) Date of Patent: Oct. 13, 2009

(54) METHOD OF MAKING ORTHOPEDIC IMPLANTS AND THE ORTHOPEDIC IMPLANTS

(75) Inventors: Amanda Martin, Norton, OH (US); Dustin Ducharme, Akron, OH (US); Lee A. Strnad, Broadview Heights, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 266 days.

(21) Appl. No.: 11/706,616

(22) Filed: Feb. 13, 2007

(65) Prior Publication Data

US 2008/0195240 A1    Aug. 14, 2008

(51) Int. Cl.
*G06F 19/00*      (2006.01)
*A61F 2/28*       (2006.01)

(52) U.S. Cl. .................. 700/98; 700/117; 700/120; 700/182; 623/16.11; 623/901

(58) Field of Classification Search .................. 700/97, 700/98, 117–120, 182, 197, 206; 703/1, 703/6, 7, 11; 623/11.11, 16.11, 17.15, 22.34, 623/22.35–22.37, 57, 901, 908, 914, 919, 623/925
See application file for complete search history.

(56) References Cited

U.S. PATENT DOCUMENTS 5,365,996 A * 11/1994 Crook .......................... 164/45
6,112,109 A * 8/2000 D'Urso ........................ 600/407
6,755,831 B2 * 6/2004 Putnam et al. .............. 606/311
6,932,842 B1 * 8/2005 Litschko et al. .......... 623/16.11
7,383,163 B2 * 6/2008 Holberg ......................... 703/6
2005/0119661 A1 * 6/2005 Hodgson et al. .............. 606/90
2005/0234563 A1 * 10/2005 Phillips ........................ 623/55
2007/0173815 A1 * 7/2007 Murase ......................... 606/53

* cited by examiner

*Primary Examiner*—Sean P Shechtman
(74) *Attorney, Agent, or Firm*—Hudak, Shunk & Farine Co., LPA

(57) ABSTRACT

The present invention relates to a method of designing an orthopedic implant in which a plurality of samples of the bone are selected and a CT scan of each of the samples of the bone is taken so that the data from the CT scan can be used to generate a 3D graphical solid body model of each of the sample of the bone. The 3D graphical models are placed into a category of one or more of average, small, and large, and the center of mass and an X, Y and Z plane for each model is determined. The 3D graphical models for one category is assembled and aligned at the center of mass to create a categorized composite 3D graphical solid body model of the bone. The categorized composite 3D graphical model is sectioned at a specified interval to create a lofted contoured surface of a selected thickness which is cut to create a categorized implant profile. The categorized implant profile is graphically fit on the categorized composite 3D graphical model and on the 3D graphical model of each of the sample of the bone in a category to check for conformity to the surface of the bone. The categorized implant profile is used to create a design of the implant.

30 Claims, 9 Drawing Sheets

Bone #4

Bone #9

Bone #24

Bone #27

Bone #31

Fully constrained the end of the Radius Bone

50-Newton Load applied at the center-of-mass axis of the radius bone and equally distributed on the orange surface.

30-degree

METHOD OF MAKING ORTHOPEDIC IMPLANTS AND THE ORTHOPEDIC IMPLANTS

FIELD OF THE INVENTION

The invention relates to a method of designing site specific orthopedic plates, and more particularly to a method of designing an orthopedic plate that mimics the topography of a bone site and which is intended for fixation to a specific part of anatomy for stabilization of a characteristic type of fracture or osteotomy.

BACKGROUND OF THE INVENTION

The paradigm for prior art orthopedic plates has involved drawing an image of the plate to suit a general outline of a site where the plate was intended to be implanted. Thus, the plate began its conception as a two dimensional representation. The final manifestation was crafted from metal and often had no, or very crude profiling in the Z direction. As this corresponded poorly with the surface of the bone that it was designed to fit, the plate was made relatively thin to allow the surgeon to contour the plate before implantation. In addition, the plate was made somewhat thin so that it could be fixed in place on the bone and that the bone itself would provide the basis of the final sculpting. This paradigm presents several problems for the attending surgeon. First, the surfaces of bone are far from flat, and the smaller the bone, the greater the relative contouring that the surgeon had to accomplish during the surgery. Second, while intact cadaveric bone can provide a basis for contouring a flexible plate, this idea is less successful with bone that has been fragmented, and the worse the break, the more difficult the reconstruction. The present invention provides the means to design orthopedic plates that can be used as the scaffolding for reconstruction of broken or deformed bone or for bones otherwise requiring orthopedic attention. The means of accomplishing the design of such a plate is the use of imaging studies of human anatomical samples to construct a generalized three dimensional solid model from which one or more computer models or resin samples can be made and which forms the basis for the three dimensional design of a corresponding orthopedic plate which is easily subject to subsequent development and design review.

In particular, the present invention uses a high-resolution model of the distal radius based on imaging studies of human anatomical samples. Samples of 16 cadaveric distal radii were harvested and high-resolution CT scans of the samples were collected and the CT data were converted to solid-part 3D models. Measurements from the cadaveric samples, CT slice images, and 3D solid part models were compared to verify the accuracy of the models. Individual models were then overlaid to create three sizes of composite models of the distal radius. In addition, simple plastic models of the samples were created using a 2-step casting process. This provided a physical correlation to the digital model for more accurately fitting the prototype plates. The current invention provides the additional advantage that the digital model created can be used for specific description of the distal radial anatomy, as well as the design and testing of fracture fixation hardware and surgical approaches and techniques since the resin castings that are created are characteristically hard and are difficult to drill or otherwise physically test.

The process described here may also be used to create similar models of other bony structures for similar end uses, including specifically small bones (i.e., below the elbow or knee, or the clavicle) and joints such as the calcaneus, the tarsals, and metatarsals, the carpals and metacarpals, the tibia, the fibula, the clavicles; long bones such as the humerus, femur, and the ulna; the vertebrae, and the pelvis and the bones of the skull.

Fractures of the distal radius are among the most common seen by orthopedic surgeons, with estimates of annual incidence ranging from 9 per 10,000 to as high as 120 per 10,000 in different populations. However, while several authors have utilized CT of the distal radius for specific diagnoses, no high-resolution model of the distal radius articular surface, epiphysis, and metaphysis based on data acquired from human materials has been reported in the literature.

In order to construct an accurate model of the distal radius, high-resolution, minimal-noise CT scans of distal radii were acquired from an immediately available selection of sixteen cadaver samples. The data from the CT scans were then used to create a composite digital model of the distal radius, which represents a composite of the models of the individual bones. This model is used in accordance with the present invention to describe in depth the typical geometry of the distal radius for design of orthopedic hardware and for injury management including surgical technique. Subsequently, the models drawn in cross section at a defined interval and a plate is constructed in a process termed "lofting" in which a cross section of plate is added at the surface of the bone (assuming to begin with that the section is rectilinear) and the plate sections are aggregated to construct a plate form which blankets the graphical bone model at its surface and which is subsequently formed to a outline that is appropriate to a particular indication. Alternatively, the outline can be selected first and the plate form can be cut in the outline shape when it is designed. In any case once the form is designed and the outline is selected, there is a plate shape design which can be used with the bone model to place fixation means, which can include all of the varieties of fixation, including but not limited to bone screws and pegs, including locking and unlocking varieties of each, K wires, wires, tensioning devices, bone anchors and adhesive. Once fixation means are added, there is plate prototype design that can be studied through computer analysis to accommodate various considerations, such as typical fractures or bone deformities, complications, problems of approach including soft tissue involvement, and loading that the implant or plate typically withstands. This easily enables the involvement of medical experts who can review electronically transmitted proposals and can comments on considerations such as the ability to capture typical fragments, fixation concerns such as impingement of fixation means on the construct or interference with soft tissue, and other issues involving ease of surgical approach and implantation. Further, it is of great assistance to make physical-models of plate and bone to allow medical advisors to play with placing the plate on the bone and suggest further advantageous adaptations. While the resin that is often used for modeling is too hard to allow for a simulation of implantation in bone, a resin model can be used to make a female mold that can be used to make a further model of artificial bone so that the medical personnel can play with the entire bone/plate/fixation construct to make additional suggestions that are incorporated into the final plate design. Thus, the method of the present invention allows far more intensive study of many aspects of the plate/bone/fixation construct enabling the possibility of better fit, ease of surgical use, better standardization for the relevant population, and better fixation and reduction eliminating possible causes of future complications, including misalignment and attendant joint pain and malfunction, and arthritis.

BRIEF DESCRIPTION OF THE INVENTION

In accordance with the invention, digital information is collected which corresponds to a sample population for a particular anatomical site. The information can be generated from known imaging techniques including CT scans, MRI or radiographic techniques. The sample may include cadavers or live specimens. The group may be defined to include particular characteristics, for example, a geriatric or pediatric population, or a generalized sample of the relevant population for a location. In particular, a representative sample of from about 4 to about 50, and more preferably from about 6 to about 30 and most preferably from about 10 to about 20 samples of a desired bone are harvested from cadavers. The cadavers are selected to give a representative sample as to variations in size. Thus, the cadavers used are of both genders, and of varying ages. The soft tissue is cleaned from the bone, attendant joints are disarticulated and the bone samples are transected. The samples are allowed to desiccate and grouped into basic categories of size. High resolution CT scans are taken as an axial section of the bone, beginning at the diaphysis and proceeding distally. Verification of the CT images is performed by comparing caliper measurements of the bone with corresponding measurements of the CT scans. All of the images are saved as DICOM files for future creation of three dimensional models and for creation of solid models. A representative model is confirmed by comparing measurements from the model with those previously taken from radius samples and from the CT scans. With the completed solid-part models grouped by size as previously described, the center of mass of each model is determined and X, Y, and Z planes defined for each individual model. The models for the six medium-sized samples are then aligned at their respective centers of mass and overlaid to produce a composite model. Composite models for the small- and large-sized groups are created in the same fashion and hard plastic models are created and used to make negative casts that permit creation of additional models. The plates are designed using a CAD program by overlaying a layer of a determined thickness on a surface of the 3-D model of the bone. Plastic prototypes are made from the projected CAD models and fitted to the plastic models of the bone. Input is solicited from engineers and surgeons and the initial implant design is adjusted to fit the indication as well as to accommodate the surgery so as to produce a final design.

BRIEF DESCRIPTION OF THE DRAWINGS

FIG. 12(a) illustrates a revised plate design viewed from the top on the distal portion of a radial bone being subjected to a load, and FIG. 12(b) illustrates the same plate design viewed from the lateral side, while FIG. 12(c) illustrates the same plate design viewed from the metacarpal articular side.

DETAILED DESCRIPTION OF THE INVENTION

Figure 1:
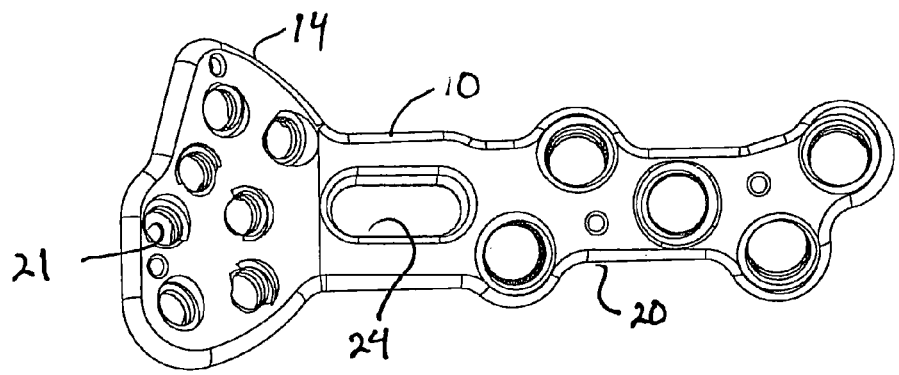
FIG. 1 is a top view of an orthopedic plate designed in accordance with the invention.
Figure 2:
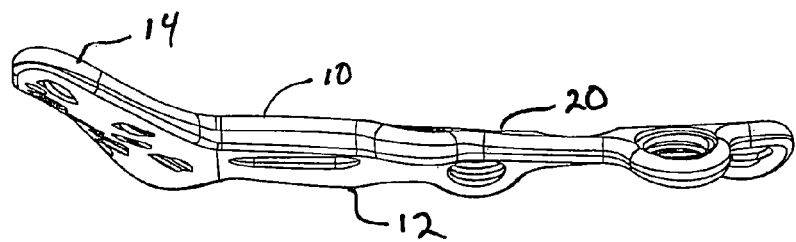
FIG. 2 is a side view of the plate of FIG. 1.
Figure 3:
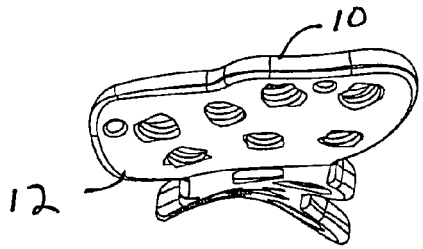
FIG. 3 is a first end view of the plate of FIG. 1.
Figure 4:
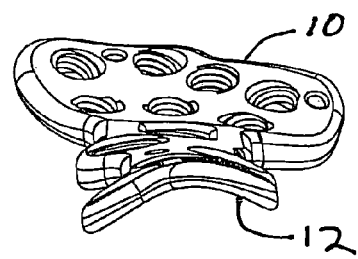
FIG. 4 is a second end view from the plate of FIG. 1.
Figure 5:
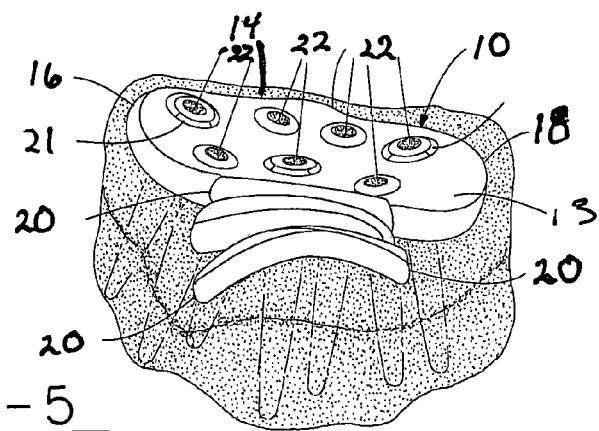
FIG. 5 is a view of the plate of FIG. 1 on a bone with pegs or screws.

In order to begin the design process of the present invention, digital information is collected for a particular anatomical site. The information can be generated from known imaging techniques including CT scans, MRI or radiographic techniques. The sample may include cadavers or live specimens. The sample group may be defined to include particular characteristics, for example, a geriatric or pediatric population, or a generalized sample of the relevant population for a location. In particular, a representative sample of from about 4 to about 50, and more preferably from about 6 to about 30 and most preferably from about 10 to about 20 samples are collected. In this instance, a sample of sixteen right distal radius specimens were harvested from preserved cadavers at Washington University School of Medicine. Six male cadavers and 10 female cadavers were used, ranging in age at time of death from 61 to 98 (Table 1). All soft tissue was stripped from the bone samples beginning at middiaphysis and working distally. The distal radioulnar and radiocarpal joints were disarticulated, and the radius was transected 10 cm proximal to the tip of the radial styloid. All remaining soft tissue was removed from the samples, and they were set aside to desiccate for three weeks before analysis. These samples were categorized, meaning that the specimens were grouped into small (5), medium (6), and large (5) based on an estimate of distal width. It should be understood that other categories could be used depending on the typical variations in shape and size of the anatomical location. For example, for some bones, the samples could be grouped into long, medium, and short, or into wide and narrow bones.

High-resolution CT images of the samples were obtained individually on a 64-detector spiral CT [Siemens]. The slice thickness was set to 0.4 mm. Samples were scanned with each CT slice as an axial section of the bone, beginning at the diaphysis and proceeding distally. Verification of the CT images was performed by comparing caliper measurements of the widest point of the distal radius samples with corresponding measurements from the CT scans (Table 2). All images were saved as DICOM files in order to allow creation of 3D reconstructions and conversion to solid-part digital models.

The data from the CT scans was inputted into a software package that reads output from a CT scan and generates a 3D model from the cross-sections given the image spacing. It is highly preferable that the model created can be read by common 3D CAD programs, such as for example, the program presently sold by SolidWorks, Corp. as "SolidWorks". In particular, the files from the CT sans were converted from the original file extension to a .vip file that could be converted by SolidWorks to a SLDPRT file or solid part file. The file for each radius that was scanned was converted to a solid part file and used to create a three dimensional graphical solid body model for each radius bone. The models were examined and it was decided how many categories to use for categorization of the individual variations. In this instance, there is sufficient variation, in particular in taking into regard gender variations, to account for a small, medium and large category of radius bone. Thus, the models were "categorized", meaning that they were separated as is appropriate to account for variations in the bone shapes and sizes. For bones, other than the distal radius, it may only be necessary to separate samples into a small and large category, and for other bones one size and shape of plate may serve for all expected individuals in a given population. Further, the bones studied were all right radius plates (and the left plates were designed as mirror images of the right plates), but it is understood that the invention could easily, and perhaps preferably, include samples scanned for both the right and the left side.

Beginning with the medium category, the center of mass was determined for each graphical model, and subsequently, X, Y, and Z planes were created for the models. All of the bones in a category were placed in an assembly in a single model and aligned at their center of mass to create a composite graphical model for that category. Drawings were created of the bones showing their critical dimensions: i.e. overall length, distal width, radial styloid location, volar tilt angle, and any other dimensions, or landmarks that might be desired during the design process. These dimensions were used to determine the sizes of plates required, the shape, (i.e., the footprint in the X, Y, direction) and the profile (ie., the topography of the plate as viewed in the Z direction).

A representative model was confirmed by comparing measurements from the model with those previously taken from radius samples and from the CT scans (Table 2). With the completed solid-part models grouped by size as previously described, the center of mass of each model was determined and X, Y, and Z planes defined for each individual model. The models for the six medium-sized samples were then aligned at their respective centers of mass and overlaid to produce a composite model or assembly. Composite models for the small- and large-sized groups were created in the same fashion.

The medium composite graphical model was subsequently sectioned at a predefined distance (i.e. about every 0.5 to about every 2 millimeter, and more preferably about every 0.75 to about every 1.25 millimeter, or more precisely about every 1 millimeter). Cross sections of the composite bone were drawn to determine planes. A lofted surface with a defined plate thickness for each individual section was created by connecting cross sectional data points to a cross-section on a plane a specified distance. The plate profile was cut into the lofted contoured surface to create a graphical plate form that corresponds to the topography of the bone. The form was fit to a determined outline to produce a plate design. This plate design was graphically placed on the composite medium bone model as well as each of the individual graphical models to check for conformity to the bone surface. Adjustments were made as desired. The fixation holes in the plates were placed using the graphical three dimensional models along with data relating to common fractures and indication and to the need for fixation and reduction. The location and angles of the fixation holes were subsequently checked by graphically modeling the plate/bone/screw construct for the composite and for individual graphical models.

Further in accordance with the invention, three-dimensional solid-part models were created for each individual radius, for the categorized composites and for the plate design. These models were SLA (sterolithography rapid prototyping) models made from PMMA resin and were created on a 3D plastic plotter. Preferably, hard plastic models were created using polymethylmethacrylate (PMMA). Negative casts were made of the original radius samples in Alginate Impression Material (ADC, Milford, Del.), with an emphasis on careful recreation of the distal end of each sample. These molds were then immediately used to make positive casts of the radii using Coralite Duz-All Self Cure Acrylic (Coralite Dental Products, Skokie, Ill.). The models were allowed to harden and cure; irregularities that arose during the casting process were removed by use of a surgical rongeur or premmer and attachments.

The plate SLA models were placed on the radius models as a verification of the contour conformity and hole location. The bones and the proposed (i.e., prototype) plate designs were supplied to advisory board surgeons for review during the design process.

Initial CT scans of our sixteen distal radius samples yielded high-resolution models of each of these samples. These scans were then converted to sixteen individual solid-part models of the samples. Verification of these models by comparison of representative measurements from the sample radii, the CT slice images, and the 3D models assures that the model is an accurate representation of the physical anatomy. After classifying these individual models into size groups based on the specific criteria of maximal distal width, high resolution models representing composites of each group were created by overlaying the individual models. This composite model is a high resolution representation of the average geometry and anatomy of the distal radius in a selected sample of cadavers.

Additionally, the present invention provides the simple and cost-effective production of hard-plastic models to serve as correlates to the digital models. These models play an important role not only in providing a tactile correlate to the radiographic data, but also allow for physical testing of reconstruction methods and hardware on exact reproductions of the sample bones. In addition, while the resin models are too hard to provide correlation to bone, they can be used to create female molds that can be used to create models from artificial bone to allow prototype plates to be attached using the proposed fixation means to further the development of the final plate design.

The method of the invention contemplates the use of a more random sample population for example as to age, gender, geographic location, and for left and right handed individuals in order to accommodate dominant and non-dominant handedness in the bone samples and in order to ensure that the model can be more widely extrapolated.

The computer image of the present invention presents several advantages. First, high resolution reconstructions for each of the each of the individual bones in the sample have been generated and measurement of numerous variables for each of these samples can be used in a description of the distal radial geometry. Second, the model reported is a direct three-dimensional composite of several samples and thus has the benefit of being somewhat "averaged" across the sample population without the limitations of a model created entirely from averaged measurements. Third, the composite model created is used for purposes beyond a geometric description of the distal radius; potential uses include design of fixation hardware, prosthesis design, and virtual manipulation to test surgical approaches and techniques. Finally, the process described here for the creation of both digital and plastic models is in no way limited to application for the distal radius; these techniques can be used for creation of models of many other structures with similar end uses.

The design methodology of the present invention presents the following advantages: it results in an implant, such as a plate or other stabilization or fixation construct, that is contoured to fit the indication; it enables the designer to strategically place fixation holes and angles; it provides a means for verification of implant fit; it provides the ability to refine the plate design through numerous iterations on the basis of the initial analysis and modeling and also to design a system of sizes and shapes that best serve the common variations in the population; the graphical and solid models provide an incredible amount of technical information that can be incorporated in design as needed; and it provides models that are easily available for use in finite element analysis (FEA).

TABLE 1

Cadaver Information

| Sample Number | Sex | Age |
|---|---|---|
| 1 | M | 78 |
| 2 | M | 91 |
| 3 | F | 77 |
| 4 | F | 95 |
| 5 | F | 87 |
| 6 | M | 61 |
| 7 | F | 98 |
| 8 | M | 78 |
| 9 | F | 85 |
| 10 | M | 83 |
| 11 | M | 89 |
| 12 | F | 88 |
| 13 | F | 94 |
| 14 | F | 84 |
| 15 | F | 85 |
| 16 | F | 73 |

TABLE 2

Measurements of Radius Sample, CT slices, and 3D Model

| Sample | Radius- Distal Width (mm) | CT Slice- Distal Width (mm) | 3D Model- Distal Width (mm) |
|---|---|---|---|
| 1 | 34.1 | 34.5 | |
| 2 | 31.8 | 31.4 | |
| 3 | 29.4 | 29.3 | 29.5 |
| 4 | 31.8 | 30.7 | |
| 5 | 34.1 | 34.2 | |
| 6 | 32.5 | 32.1 | |
| 7 | 31.8 | 32.1 | |
| 8 | 29.4 | 29.3 | |
| 9 | 32.5 | 31.4 | |
| 10 | 33.3 | 33.5 | |
| 11 | 33.3 | 33.5 | |
| 12 | 30.2 | 29.3 | |
| 13 | 32.5 | 32.8 | |
| 14 | 31.8 | 32.1 | |
| 15 | 32.5 | 32.1 | |
| 16 | 32.5 | 32.8 | |
| Mean | 32.1 | 31.9 | |
| standard Dev. | 1.4 | 1.7 | |

Radius width was measured using calipers at the widest point on the distal radius. CT slice width was measured as the width of the widest slice acquired within the distal radius. Model width was measured using the "measure" tool in Solid-Works, finding the maximum width at the distal radius when viewed from the volar perspective.

A distal radius plate designed in accordance with the method of the invention is shown at 10 in FIGS. 1-5. The plate includes a surface 12 which faces, and may at least partially be in contact with, the bone surface. The plate also includes a surface 13 that faces outward from the bone surface. A distal portion 14 of the plate 10 is intended to support the distal most portion of the radius bone. The distal portion includes a side 16 that supports the radial styloid and an opposite side 18. In addition, the plate includes a proximal plate-like portion 20 that spirals along the long axis of the radial bone as can be seen in particular in FIGS. 3 through 5. In addition, the distal portion includes holes 21 for pegs or screws 22, which support the distal portion of the radius. These holes can be threaded for locking screws, or can be free from threads or a locking mechanism. They can also incorporate a variable locking mechanism as is known in the art. The plate portion also includes holes for fixation means, including for example, screws and k-wires. The plate may include other features as are found to be advantageous, such as the sliding slot 24 shown in the proximal portion of the plate.

Figure 6:
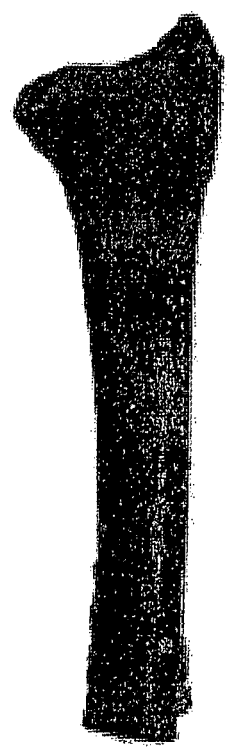
FIG. 6(a) is a representation of the distal portion of a radial bone.
FIG. 6(b) is a three dimensional graphic representation of the bone.
Figure 6:
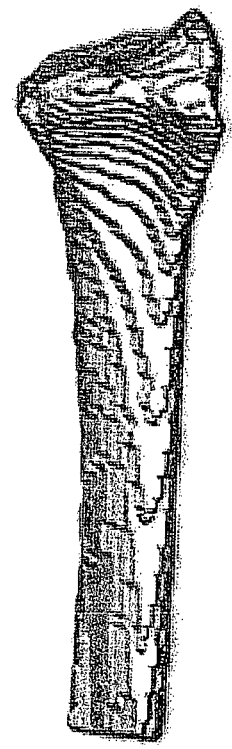
Figure 7:
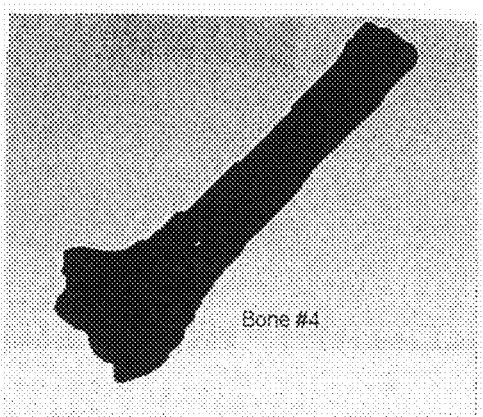
FIGS. 7(a)-7(e) are three dimensional graphical representations of the distal portions of individual radial bones.
Figure 7:
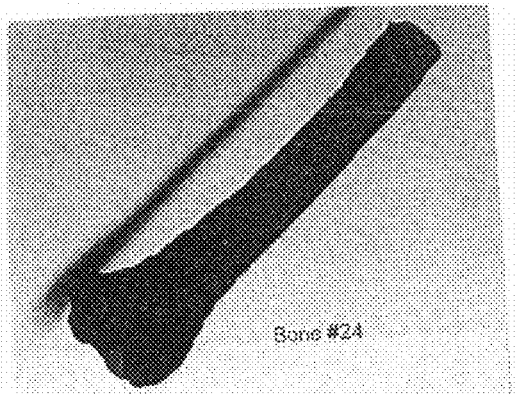
Figure 7:
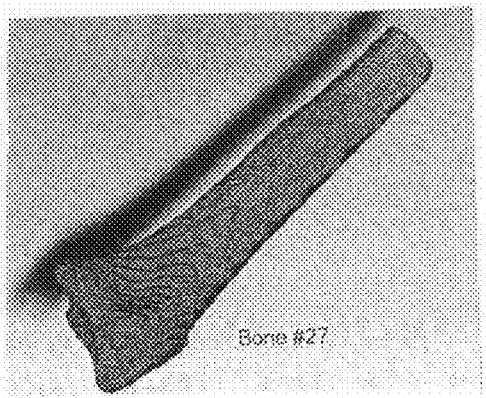
Figure 7:
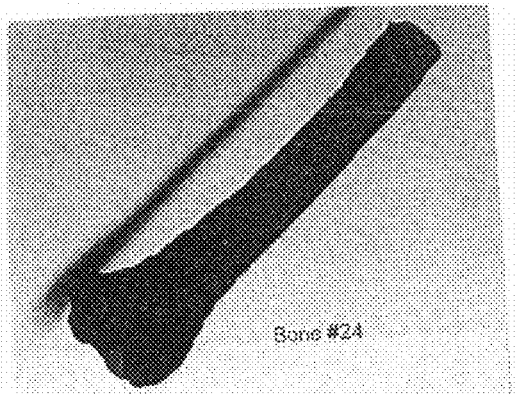
Figure 7:
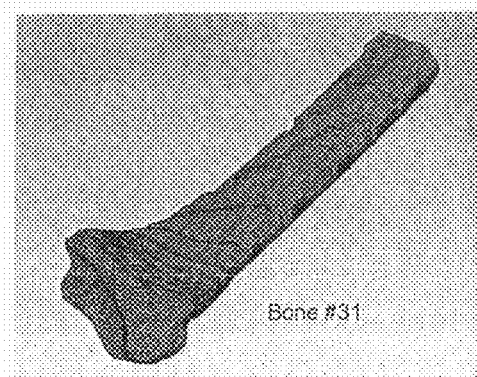
Figure 8A:
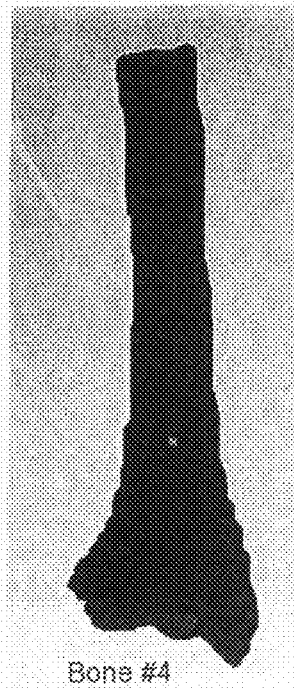
FIGS. 8(a)-8(e) are three dimensional graphical representations of the volar surfaces of distal portions of individual radial bones.
Figure 8B:
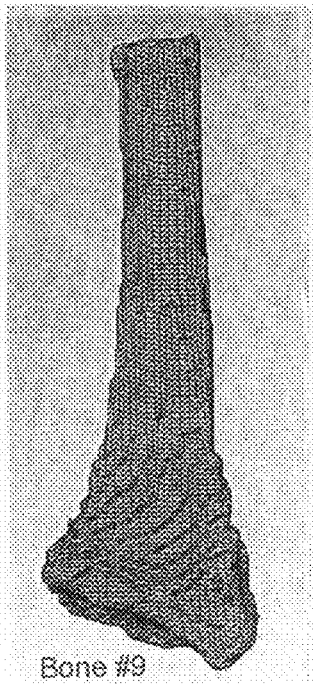
Figure 8C:
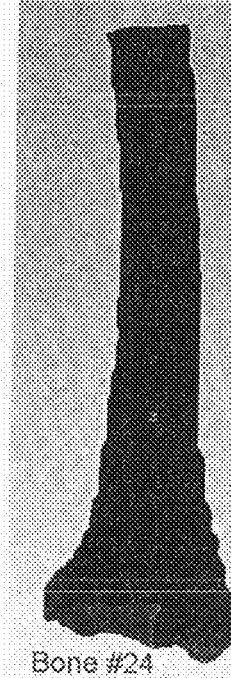
Figure 8D:
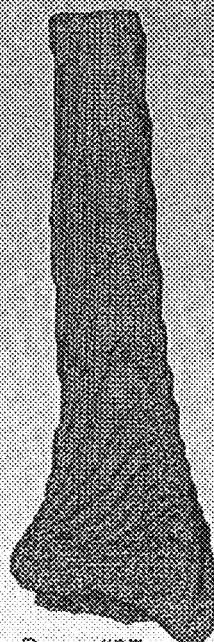
Figure 8E:
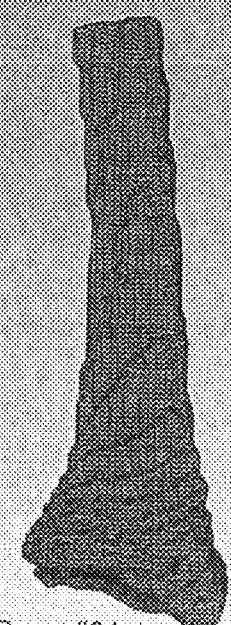
Figure 9:
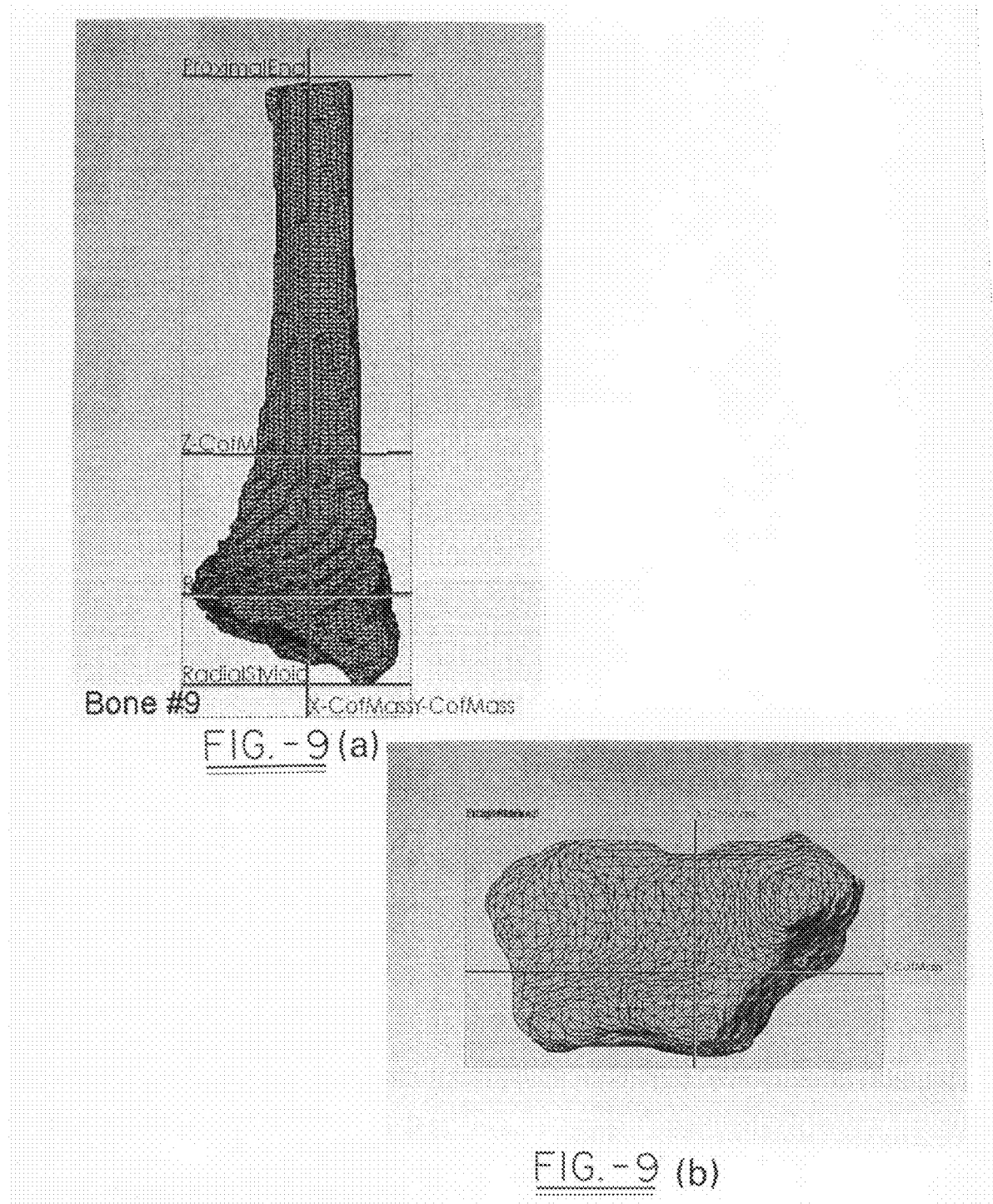
FIG. 9(a) is an illustration of the three dimensional representation of the composite model of the distal portion of a radial bone viewed at the volar surface.
FIG. 9(b) is the same model viewed from the distal articular surfaces.
Figure 10:
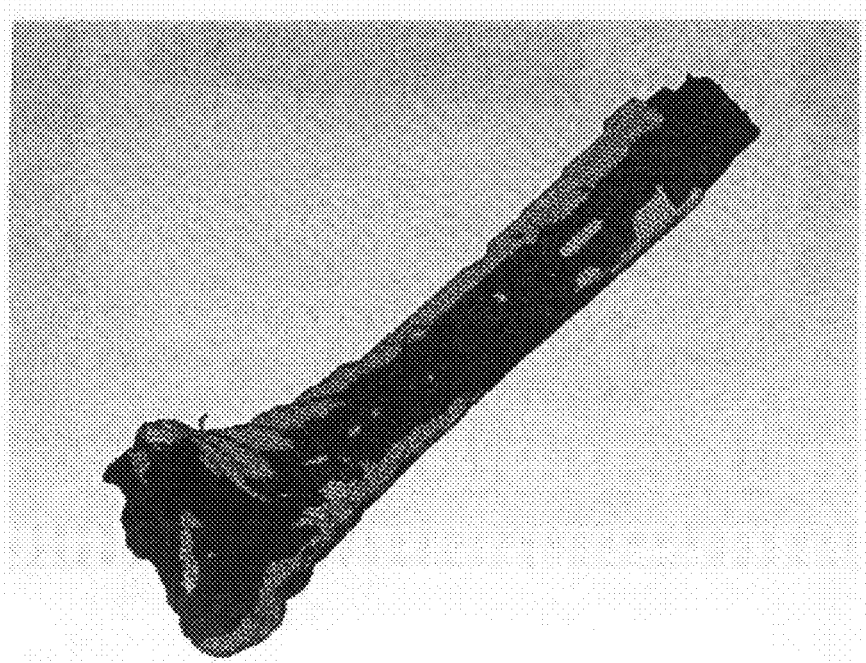
FIG. 10(a) is an illustration of the three dimensional representation of the composite model of the distal portion of a radial bone in a medial/volar view.
FIG. 10(b) illustrates a corresponding plate design.
Figure 10:
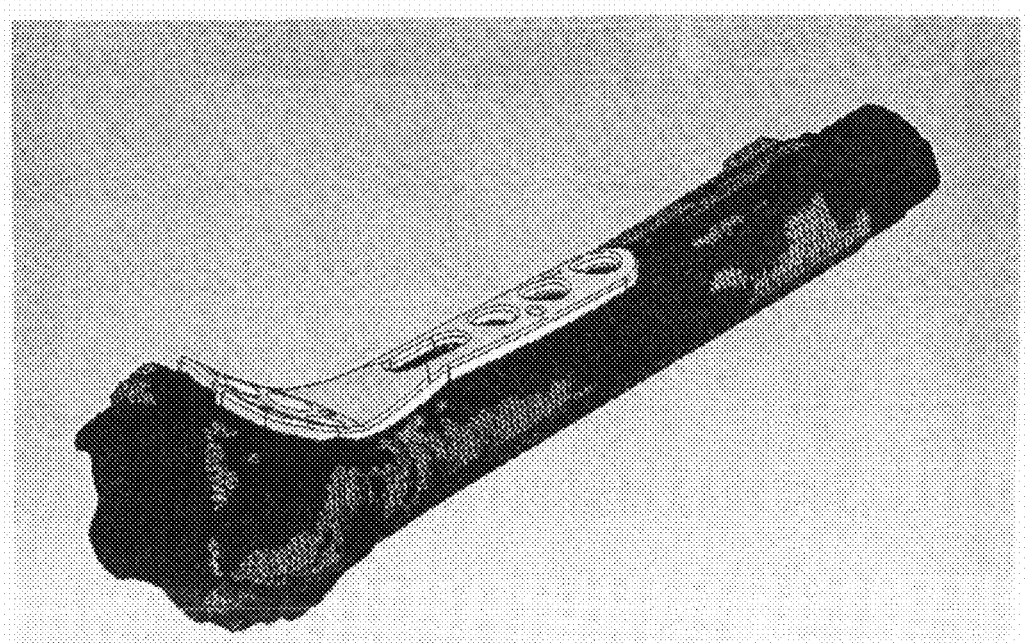
Figure 11A:
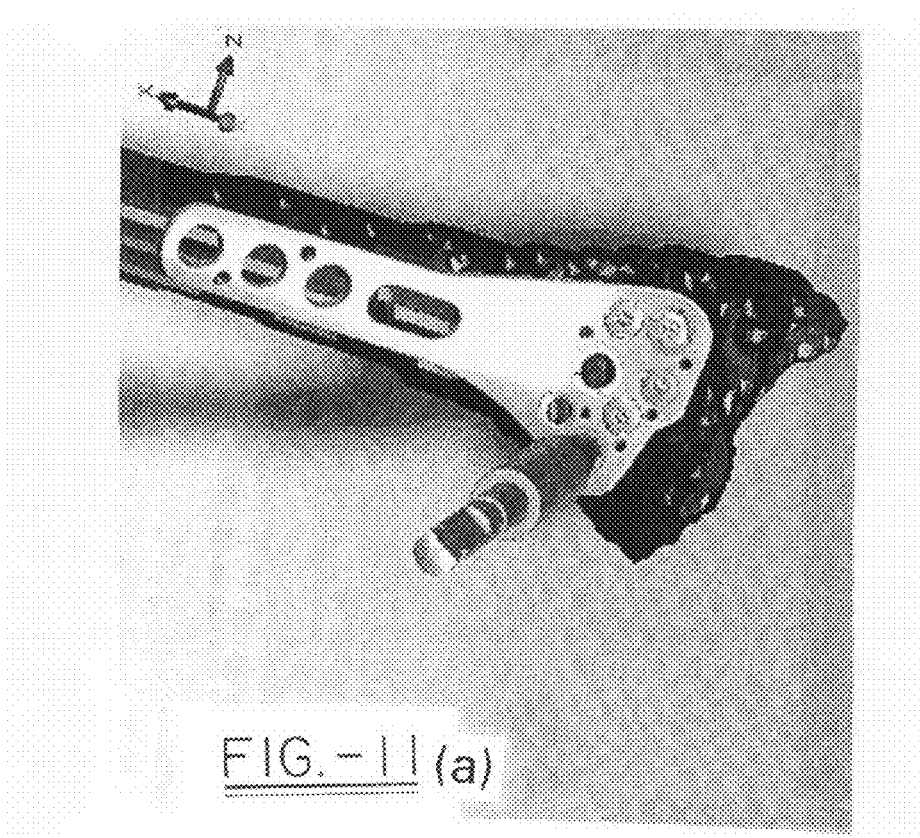
FIGS. 11(a) and 11(b) is an illustration of an initial design of the plate with pegs and a drill guide, taken from the top and from the side.
Figure 11B:
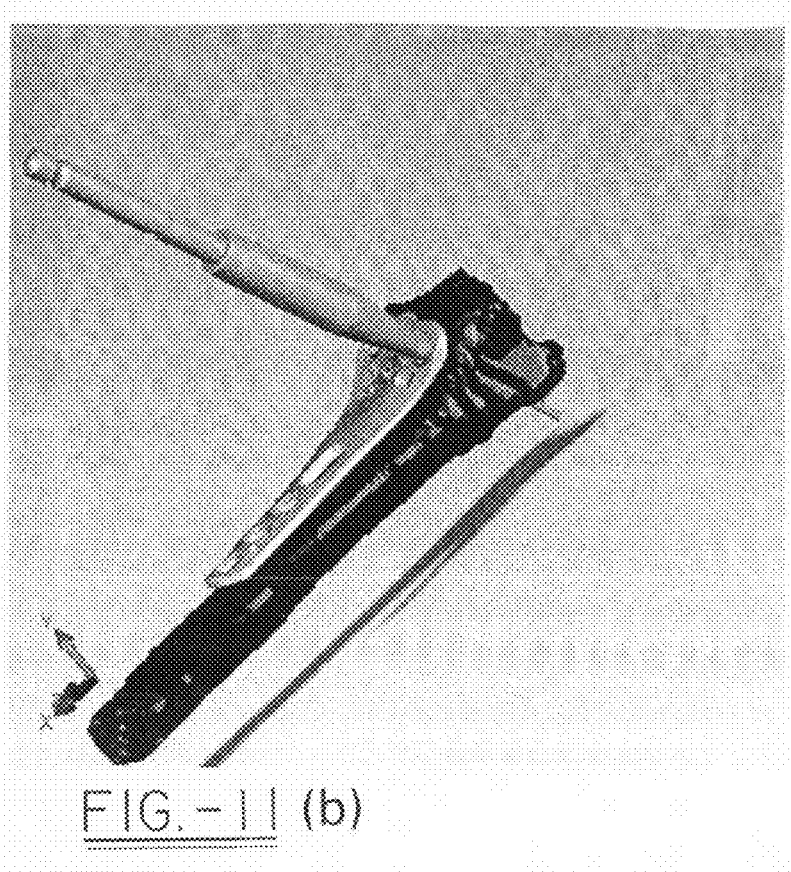
Figure 12:
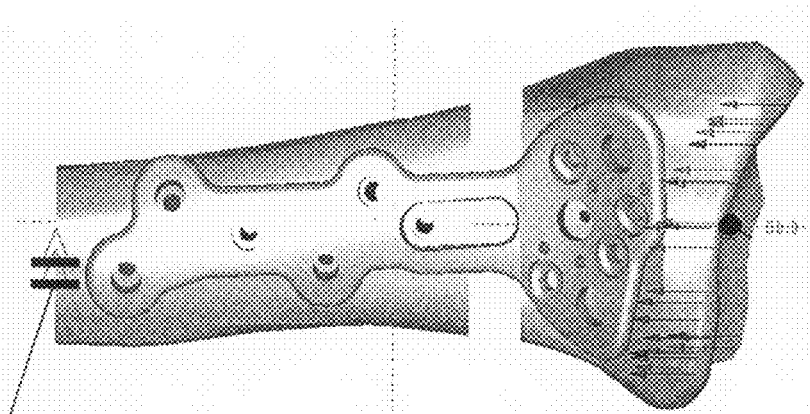
Figure 12B:
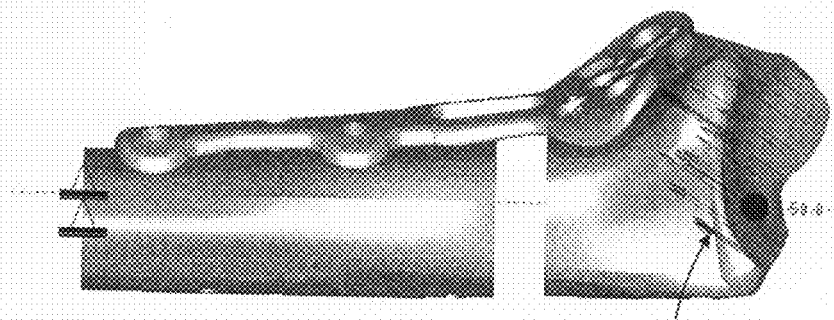
Figure 12:
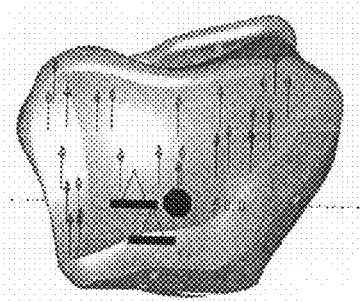
Figure 13A:
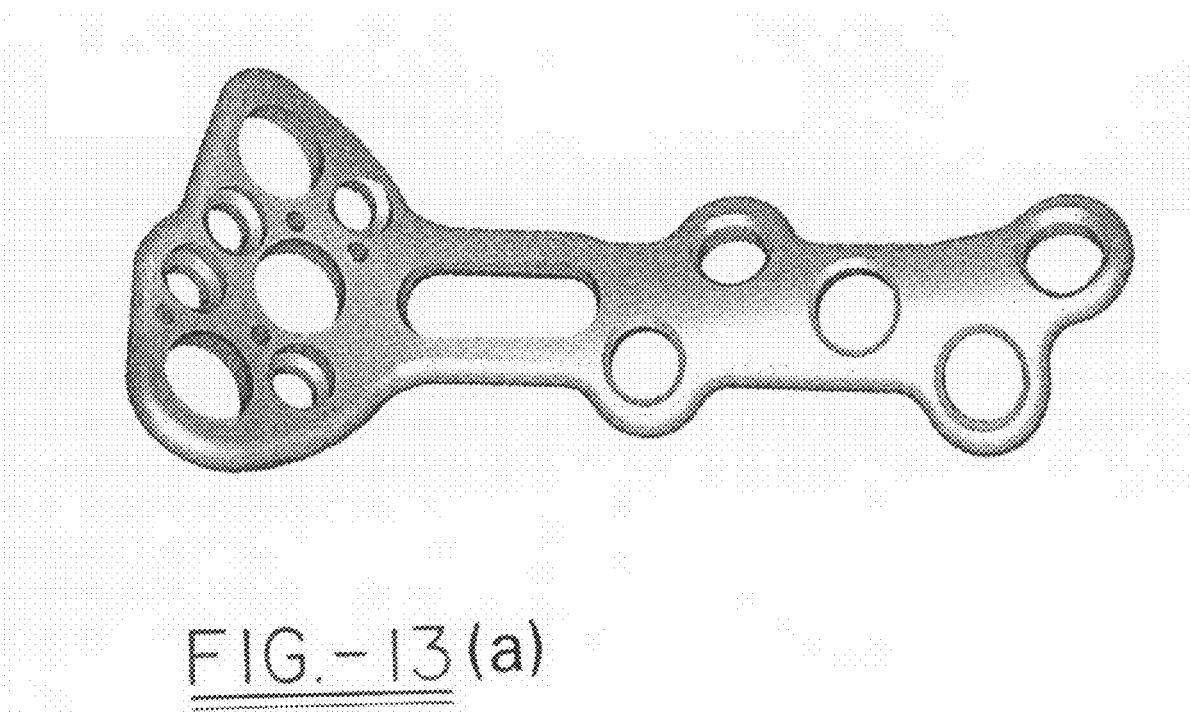
FIG. 13(a) is a further iteration of a plate design showing a revision to accommodate variable locking pegs and FIG. 13(b) is a view of the further iteration showing the placement and angulation of the fixation means.
Figure 13B:
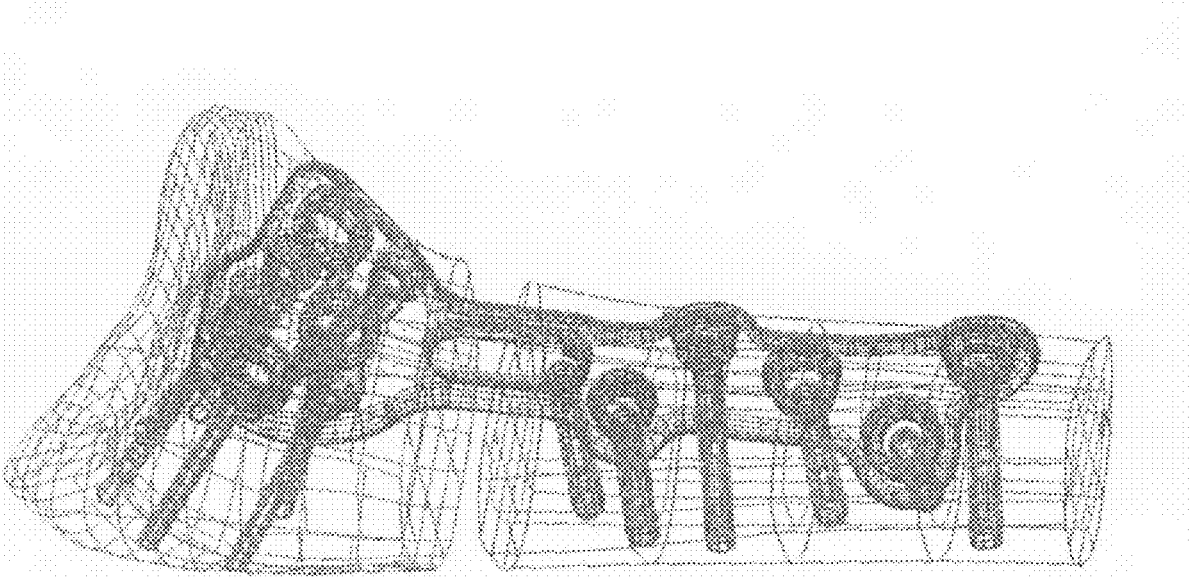

FIG. 6(a) illustrates a cadaveric sample of a distal radius, and FIG. 6(b) illustrates a corresponding 3D model for that bone sample. FIGS. 7(a) through 7(e) illustrate the development of graphical models for individual bone samples and FIGS. 8(a) through 8(e) illustrates the views of the graphical models of the volar surfaces. FIGS. 9(a) and 9(b) illustrate the alignments of the bones at the center of mass to allow a composite model to be assembled. FIG. 10(a) illustrates the composite graphical model with the bones of one of the small, medium or large category aligned at the centers of mass. FIG. 10(b) shows a lofted plate sections that have been assembled into a shape to simulate a first plate design. FIGS. 11(a) and 11(b) illustrate the addition of both screws and instruments (in this case a drill guide) to the construct. FIG. 11(a) illustrates the design with the screws from the top, and FIG. 11(b) illustrates a view from the medial side of the radius. This view further shows the placement and angles of the peg members which are used to fix fragments of the distal portion of the radius. FIGS. 12(a) through 12(c) illustrate a second design of the plate with loading at the center of mass axis of the radius bone and equally distributed at the surface of the plate. In FIG. 12(b), the load is applied at a 30° angle to the longitudinal axis. The load is applied along the Y axis in FIG. 12(c). FIG. 13(a) shows a further iteration of the plate design with enlarged holes for a variable locking mechanism. The placement, angles and length of bone screws and pegs are shown in FIG. 13(b) which has been tested using FEA analysis to determine stress and deflection profiles.

While in accordance with the patent statutes the best mode and preferred embodiment have been set forth, the scope of the invention is not limited thereto, but rather by the scope of the attached claims.

What is claimed is:

1. A method of making an orthopedic implant for a bone comprising the steps of
    selecting a plurality of samples of the bone and taking a CT scan of each of the samples of the bone;
    using the output from the CT scan to generate a 3D graphical solid body model of each of the samples of the bone;
    placing the 3D graphical models into a category of one or more of a first category, a second category and a third category, determining the center of mass for each 3D graphical model, and generating an X, Y and Z plane for each model;
    placing the 3D graphical models for one category into an assembly and aligning each of the 3D graphical models in that category at the center of mass to create a categorized composite 3D graphical solid body model of the bone;

forming a plurality of cross sections of the categorized composite 3D graphical model and building cross sections which are assembled to create a lofted contoured surface and cutting the lofted contoured surface to create a categorized implant form;

fitting the categorized implant form on the categorized composite 3D graphical model and on the 3D graphical model of each of the samples of the bone in a category to check for conformity to the surface of the bone;

using the categorized implant form to create a design of the implant; and using the design of the implant to make the implant.

2. A method as set forth in claim 1 further including the step of creating a drawing of the categorized composite 3D graphical model for use to determine one or more of the size or the profile of the implant.

3. A method as set forth in claim 1 wherein the implant further includes fixation holes and the method further includes the step of using data of common fractures of the bone and of the need for fixation and reduction to determine the location and angles of the fixation holes in the implant.

4. A method as set forth in claim 2 wherein the method further includes the step of creating a physical model of the bone using the categorized composite 3D graphical model.

5. A method as set forth in claim 4 wherein the physical model of the bone comprises plastic and is created using a 3D plastic plotter.

6. A method as set forth in claim 5 wherein a physical model is created for each of the samples of the bone in each of the first size category, the second size category and the third size category.

7. A method as set forth in claim 6 wherein the method further includes the step of creating a physical model of the implant using the categorized implant form and wherein the physical model of the implant comprises plastic and is made using stereolithoaraphy.

8. A method as set forth in claim 7 wherein the physical model of the implant is fit on the physical model for each of the samples of the bone in the first size category, the second size category and the third size category.

9. A method as set forth in claim 8 further including the step of adjusting the design of the implant based on the results of the fit of the physical model of the implant on the physical model of one or more of the categorized composite 3D graphical solid body model of the bone or on the physical model of one of the samples of the bone in the first size category, the second size category and the third size category.

10. A method as set forth in claim 9 wherein the implant has a contour and the adjustment to the design includes a change in the contour of the implant.

11. A method as set forth in claim 9 wherein the implant has a profile and the adjustment to the design includes a change in the profile of the implant.

12. A method as set forth in claim 9 wherein the implant includes fixation holes and the adjustment to the design includes a change in the placement of the fixations holes.

13. A method as set forth in claim 9 wherein the implant includes fixation holes and the adjustment to the design includes a change in the angle of the fixations holes.

14. A method as set forth in claim 1 wherein the categorized composite 3D graphical solid model of the bone is used for a finite element analysis.

15. A method as set forth in claim 1 wherein the physical model of the bone is used for a finite element analysis.

16. A method as set forth in claim 14 wherein the categorized composite 3D graphical solid model of the bone is modified to simulate a fracture of the bone, and a categorized 3D graphical model of the implant is made and incorporated onto the categorized composite 3D graphical model of the bone to create a 3D graphical construct of a fractured bone with an implant and the 3D graphical construct is subjected to loads.

17. A method as set forth in claim 16 wherein the loads are applied in directions and magnitudes to simulate normal human activity and the stress and displacement of the implant is monitored to generate information for optimization of the implant.

18. A method as set forth in claim 17 wherein the information generated from the applied loads is used to optimize the design of the implant.

19. A method of making a plate for a one or more of a bone comprising the steps of selecting a plurality of samples of the bone and taking a digital imaging scan of each of the samples of the bone and using the output from the digital imaging scan to generate a 3D graphical solid body model of each of the samples of the bone;

determining the center of mass for each 3D graphical model, and generating an X, Y and Z plane for each model relative to the center of mass and aligning each of the 3D graphical solid body models at the center of mass and in the X, Y, and Z planes to create a composite 3D graphical solid body model of the bone;

using the composite 3D graphical model to create a graphical bone plate profile;

graphically fitting the graphical bone plate profile on the composite 3D graphical model and on the 3D graphical model of each of the samples of the bone to check for conformity of the bone plate profile to the surface of the bone;

using the graphical bone plate profile to create a design of the bone plate; and using the design of the bone plate to make a bone plate.

20. A method as set forth in claim 19 further including the step of sorting the 3D graphical solid body models into the categories of a first size having a first distal width, a second size having a second distal width and a third size having a third distal width, the first distal width being larger than the second distal width and small than the third distal width.

21. A method as set forth in claim 19 wherein the bone plate further includes fixation holes and the method further includes the step of using data of common fractures of the bone to determine the location and angles of the fixation holes in the bone plate.

22. A method as set forth in claim 21 wherein the method further includes the step of creating a physical model of the bone using the composite 3D graphical model.

23. A method as set forth in claim 22 wherein the physical model of the bone comprises resin, plastic or artificial bone.

24. A method as set forth in claim 19 wherein the method further includes the step of creating a prototype model of the bone plate using the bone plate profile.

25. A method as set forth in claim 19 wherein a physical model is created for each of the samples of the bone.

26. A method as set forth in claim 24 wherein the design of the bone plate is created in a right and a left version.

27. A method as set forth in claim 25 further including the step of creating a physical model of the bone plate using the graphical bone plate profile and wherein the physical model of the bone plate is fit on a plurality of physical models of the bone.

28. A method as set forth in claim 27 further including the step of making a design adjustment to the design of the bone plate based on the results of the fit of the physical model of the bone plate on the physical model of one or more of the composite 3D graphical solid body model of the bone or on the physical model of one of the samples of the bone.

29. A method as set forth in claim 28 wherein the design adjustment to the bone plate includes a change in the contour or the profile of the bone plate.

30. A method as set forth in claim 28 wherein the bone plate includes fixation holes which accept screws or pegs, and the adjustment to the design includes a change in the placement or the angle of the fixations holes.

* * * * *